United States Patent
Chen et al.

(10) Patent No.: US 10,539,633 B2
(45) Date of Patent: Jan. 21, 2020

(54) ULTRAHIGH RESOLUTION MAGNETIC RESONANCE IMAGING METHOD AND APPARATUS

(71) Applicant: SHANGHAI INSTITUTE OF MICROSYSTEM AND INFORMATION TECHNOLOGY, CHINESE ACADEMY OF SCIENCES, Shanghai (CN)

(72) Inventors: Lei Chen, Shanghai (CN); Zhen Wang, Shanghai (CN); Xiaoming Xie, Shanghai (CN); Mianheng Jiang, Shanghai (CN)

(73) Assignee: SHANGHAI INSTITUTE OF MICROSYSTEM AND INFORMATION TECHNOLOGY, CHINESE ACADEMY OF SCIENCES, Shanghai (CN)

( * ) Notice: Subject to any disclaimer, the term of this patent is extended or adjusted under 35 U.S.C. 154(b) by 361 days.

(21) Appl. No.: 15/315,453

(22) PCT Filed: Dec. 18, 2014

(86) PCT No.: PCT/CN2014/094175
§ 371 (c)(1),
(2) Date: Dec. 1, 2016

(87) PCT Pub. No.: WO2015/184761
PCT Pub. Date: Dec. 10, 2015

(65) Prior Publication Data
US 2017/0102440 A1    Apr. 13, 2017

(30) Foreign Application Priority Data
Jun. 3, 2014 (CN) .......................... 2014 1 0242678

(51) Int. Cl.
*G01R 33/32* (2006.01)
*G01R 33/385* (2006.01)
(Continued)

(52) U.S. Cl.
CPC ............ *G01R 33/326* (2013.01); *A61B 5/055* (2013.01); *G01N 24/08* (2013.01); *G01R 33/385* (2013.01);
(Continued)

(58) Field of Classification Search
CPC .. G01R 33/326; G01R 33/385; G01R 33/445; G01N 24/08; A61B 5/055; A61B 2560/0223
(Continued)

(56) References Cited

U.S. PATENT DOCUMENTS 5,351,006 A * 9/1994 Sumanaweera .. G01R 33/56563
324/307
2009/0087064 A1* 4/2009 Barbic .................. A61B 6/504
382/131
(Continued)

FOREIGN PATENT DOCUMENTS

| CN | 1643403 A | 7/2005 |
|---|---|---|
| CN | 102068256 A | 5/2011 |

(Continued)

OTHER PUBLICATIONS

Longenecker, Jonilyn G., et al. "High-gradient nanomagnets on cantilevers for sensitive detection of nuclear magnetic resonance." ACS nano 6.11 (2012): 9637-9645. (Year: 2012).*
(Continued)

*Primary Examiner* — Christopher P McAndrew
(74) *Attorney, Agent, or Firm* — Global IP Services; Tianhua Gu (57) ABSTRACT
An ultrahigh resolution magnetic resonance imaging method and apparatus, the method comprises the following steps of:
(Continued)

placing a test sample within an action range of a magnetic gradient source and a nano-scale superconducting quantum interference device, applying a static magnetic field on the test sample by a static magnetic source, and applying a nuclear magnetic resonance radio-frequency pulse on the test sample by a radio-frequency source to excite the test sample to cause nuclear magnetic resonance; directly coupling the nano-scale superconducting quantum interference device with the test sample to detect nuclear magnetic resonance spectrum signals generated by the test sample; establishing an image of the test sample according to the detected nuclear magnetic resonance spectrum signals and space distribution information of gradient magnetic fields generated by the magnetic gradient source.

15 Claims, 4 Drawing Sheets

(51) Int. Cl.
    *A61B 5/055*     (2006.01)
    *G01R 33/44*     (2006.01)
    *G01N 24/08*     (2006.01)

(52) U.S. Cl.
    CPC .... *G01R 33/445* (2013.01); *A61B 2560/0223* (2013.01)

(58) Field of Classification Search
    USPC .......................................................... 324/309
    See application file for complete search history.

(56) References Cited

U.S. PATENT DOCUMENTS

| | | | | |
|---|---|---|---|---|
| 2010/0097056 | A1* | 4/2010 | Lam .................... | G01R 33/0354 324/228 |
| 2010/0289491 | A1* | 11/2010 | Budker .................. | G01R 33/26 324/304 |
| 2010/0301854 | A1* | 12/2010 | Rugar .................... | B82Y 35/00 324/307 |
| 2011/0068789 | A1* | 3/2011 | Hwang .............. | G01R 33/3804 324/307 |
| 2011/0077501 | A1* | 3/2011 | Rofougaran ........ | G06F 19/3418 600/410 |
| 2013/0278265 | A1* | 10/2013 | Kim ..................... | G01R 33/445 324/318 |

FOREIGN PATENT DOCUMENTS

| | | |
|---|---|---|
| CN | 103616650 A | 3/2014 |
| JP | 2005137411 A | 6/2005 |
| JP | 2012000222 A | 1/2012 |
| WO | WO 9503550 | 2/1995 |

OTHER PUBLICATIONS

McDermott, Robert, et al. "SQUID-detected magnetic resonance imaging in microtesla magnetic fields." Journal of low temperature physics 135.5-6 (2004): 793-821. (Year: 2004).*

* cited by examiner

ULTRAHIGH RESOLUTION MAGNETIC RESONANCE IMAGING METHOD AND APPARATUS

CROSS REFERENCE TO RELATED PATENT APPLICATION

The present application is the US national stage of PCT/CN2014/094175 filed on Dec. 18, 2014, which claims the priority of the Chinese patent application No. 201410242678.0 filed on Jun. 3, 2014, which applications are incorporated herein by reference.

BACKGROUND OF THE PRESENT INVENTION

Field of Invention

The present invention belongs to a magnetic resonance imaging field, and relates to an ultrahigh resolution magnetic resonance imaging method and apparatus.

Description of Related Arts

A magnetic resonance imaging (MRI) apparatus is an imaging diagnosis apparatus that excites nuclear spins of a test body placed in a superposition of a static magnetic field and a gradient magnetic field by a radio frequency (RF) signal corresponding to their Larmor frequency, and to reconstruct an image according to the magnetic resonance (MR) signal generated with the excitation and space distribution information of the gradient magnetic field.

The magnetic resonance imaging technology has become a necessary diagnostic tool for modern medical diagnosis, since it may carry out non-destructive imaging on a human body. It utilizes the theory of nuclear magnetic resonance, and adopts a method that adds the gradient magnetic field to obtain the space position information of the nuclear spin according to the corresponding relation between the nuclear magnetic resonance frequency and a magnitude of the magnetic field. Since the nuclear spins inherently have relative lower polarizability, and on the assumption that the nuclear spin density is constant, only the sample with relative larger volume is able to obtain sufficient spin polarization to generate a reasonable signal. As a result, the magnetic resonance imaging resolution is limited and remains at the order of millimeter. Therefore, it requires for improving two basic factors to improve the magnetic resonance imaging resolution to detect the microscopic world, wherein, one is to improve the magnetic field gradient, and another having a higher difficulty level is to improve the detecting sensibility of the spins.

Currently, a magnetic resonance force microscopy (MRFM), which utilizes a very sensitive cantilever to detect force interaction between spins and a nanomagnet, may achieve a magnetic resonance imaging with a resolution of 4~6 nanometers. Since such detection technology is to transform the spin physical quantity into a weak force measurement through its interaction with the nanomagnet, and thus is highly susceptible to disturbance of other environmental factors, such as an electric field force, thermal fluctuation, ambient mechanic vibration, etc. Meanwhile, it has been proposed a conception of using a nitrogen-vacancy center (NV center) in a diamond as a ultra-sensitive spin detector to achieve a nano-magnetic resonance imaging in recent years, while there are still many technical difficulties to be solved, such as, the NV center in the diamond fails to work in a relative larger magnetic field environment, with the result that it is impossible to highly polarize the nuclear spins of the test body to generate relative larger signals. Besides, the NV center is generally located inside the diamond, and is thus relative far away from the surface, while its coupling effect with the spins quickly attenuates with distance, thus its imaging scope is also relative small.

A Chinese patent, with a publication number of CN1643403A, has disclosed a NMR (nuclear magnetic resonance) and a MRI (magnetic resonance imaging) detected under a extremely low field SQUID (superconducting quantum interference device), which utilizes the SQUID of high sensitivity to measure the spin signal under a extremely low magnetic field. The working principle thereof is that: transforming a spin signal of an atom into a current signal by a pickup coil, transforming the current signal into a magnetic signal, and utilizing the SQUID to measure the signal, wherein, the SQUID actually plays a role of an amplifier of the current signal. In such method, the sample is separated with the SQUID, that is, the sample is at room temperature, and the SQUID is isolated below the superconducting critical temperature; since the conventional SQUID is susceptible to the effect of environmental magnetic field, generally in practice, the SQUID is packaged in magnetically shielding environment, and the magnetic signal of the sample is transferred to the SQUID through the pickup coil, which is also a commonly used measurement arrangement of the conventional SQUID. The main advantage of the MRI imaging by ultra-low field SQUID in the patent is to cancel the dependence of the MRI on a huge static magnetic field $B_0$, thereby it is achievable to utilize the earth magnetic field as a MRI imaging condition. Unfortunately, although the measurement arrangement of the conventional SQUID has much higher sensitivity than that of a detector used in a commercial MRI apparatus, due to the limitation of the pickup coil, most magnetic signals of the sample are lost during the transfer process. Therefore, when measuring a tiny sample or microscopic spins, the conventional SQUID detector may not greatly exhibit its full potential.

The nano-scale superconducting quantum interference device (nanoSQUID) is a novel device developed based on the conventional SQUID, which utilizes a nano junction to replace a conventional tunnel junction, so that the area of the superconducting ring can be greatly decreased, and coupling degree between the device and the tiny sample can be greatly enhanced. As comparing to the magnetic resonance force microscopy and the NV center in the diamond, the nano-scale superconducting quantum interference device (nanoSQUID) features comparative or better spin sensitivity. Moreover, the device performs direct and close range detections by a magnetic flux coupling, which is not influenced by vibrations and electric field; besides, the device may be normally operated under a strong magnetic field, which means the thermal equilibrium polarization of the nuclear spins can be increased by an external static magnetic field. Therefore, the magnetic resonance imaging of nano-scale resolution is achievable by utilizing the nanoSQUID as a detector and by cooperating with a large gradient magnetic field.

SUMMARY OF THE PRESENT INVENTION

In view of the above disadvantages in the prior art, an object of the present invention is to provide an ultrahigh resolution magnetic resonance imaging method and apparatus, to solve the problems in the prior art that the resolution of the magnetic resonance imaging is relative low, and the method and apparatus in the prior art are susceptible to the disturbance of other environmental noise or only work in a small magnetic field environment and have relative small imaging scope, etc.

In order to achieve the above object and other related objects, the present invention provides an ultrahigh resolution magnetic resonance imaging method, which at least comprises the following steps of:

placing a test sample within an action range of a magnetic gradient source and a nano-scale superconducting quantum interference device, applying a static magnetic field on the test sample by a static magnetic source, and applying a nuclear magnetic resonance radio-frequency pulse on the test sample by a radio-frequency source to excite the test sample to cause nuclear magnetic resonance;

directly coupling the nano-scale superconducting quantum interference device with the test sample to detect nuclear magnetic resonance spectrum signals generated by the test sample;

establishing an image of the test sample according to the detected nuclear magnetic resonance spectrum signals and space distribution information of gradient magnetic fields generated by the magnetic gradient source.

Alternatively, the method for detecting the nuclear magnetic resonance spectrum signals generated by the test sample by using the nano-scale superconducting quantum interference device is that: inputting a predetermined current pulse to the nano-scale superconducting quantum interference device to make it work at an operating point; if the nuclear magnetic resonance spectrum signals of the test sample is coupled to the nano-scale superconducting quantum interference device, magnetic flux will be changed, to deviate the nano-scale superconducting quantum interference device from the operating point; using a programmable logic circuit to perform a PID feedback logic operation, and applying a feedback signal on the nano-scale superconducting quantum interference device through a feedback coil controlled by a current source, to fix the nano-scale superconducting quantum interference device back to the operating point; and obtaining the nuclear magnetic resonance spectrum signals of the test sample by measuring feedback quantity of the feedback circuit.

Alternatively, a continuous radio-frequency source is adopted, and a mixer or modulator is used, to combine with a baseband signal to form a combined nuclear magnetic resonance pulse, and to generate a radio-frequency magnetic field at a radio-frequency source terminal, to excite the test sample.

Alternatively, position measurement is performed by scanning a frequency of the static magnetic field or the radio-frequency magnetic field, to instantly obtain the nuclear magnetic resonance spectrum signals in a resonance region.

Alternatively, the magnetic gradient generated by the magnetic gradient source is 0.05~5 mT/nm.

Alternatively, a distance between the nano-scale superconducting quantum interference device and the test sample is less than 100 nm.

Alternatively, the magnetic gradient source is obtained by a current flowing through a nanowire, and the nanowire has a width of 100 nm~1 μm.

Alternatively, the magnetic gradient source is a nanomagnet, and the nanomagnet has an end size of 100 nm~1 μm.

Alternatively, the magnetic gradient source generates a three-dimensional gradient magnetic field or a two-dimensional gradient magnetic field.

The present invention further provides a magnetic resonance imaging apparatus, comprising:

a static magnetic source, for forming a static magnetic field in a space where the test sample locates;

a radio-frequency source, for exciting the nuclear magnetic resonance of the test sample;

a magnetic gradient source, for forming a gradient magnetic field in the space where the test sample locates;

a detector, which is a nano-scale superconducting quantum interference device, for directly coupling the test sample to detect the nuclear magnetic resonance spectrum signals generated by the nuclear spins of the test sample;

an image forming apparatus, for constructing an image of the test sample according to the nuclear magnetic resonance spectrum signals detected by the detector.

Alternatively, the magnetic gradient source is a nanowire or nanomagnet.

Alternatively, the magnetic gradient source is a nanowire; the magnetic gradient source, the radio-frequency source and the detector are integrated on a same chip.

Alternatively, a superconducting ring of the nano-scale superconducting quantum interference device has an area less than 1 μm$^2$.

Alternatively, the magnetic resonance imaging apparatus has a resolution of 1~100 nm.

Alternatively, the coupling distance between the detector and the test sample is less than 100 nm.

From the above, the magnetic resonance imaging method and apparatus of the present invention, has the following beneficial effects that: the present invention adopts the nano-scale superconducting quantum interference device (nanoSQUID) as a detector for the nuclear magnetic resonance (NMR) spectrum signal in the magnetic resonance imaging (MRI), to achieve the magnetic resonance imaging of nano-scale resolution. Because the area of the superconducting ring of the nano-scale superconducting quantum interference device is relative small, the device is not susceptible to the disturbance of external magnetic field, vibrations and electric signals, and is not need for individual magnetic shielding isolation; the test sample may be directly and close-range coupled with the detector or directly contacted with the detector, and together cooled to below its superconducting critical temperature, thereby the imaging scope is relative large, and the performance for characterizing magnetic properties of the microscopic sample and detecting the microscopic spins is prominent, and thus the measurement sensitivity of single-electron spins is achievable. Meanwhile, the nano-scale superconducting quantum interference device can withstand a relative large parallel critical magnetic field because of its planar structure, and can work in a strong magnetic field. Meanwhile, assuming that the number of spins is constant, the strong magnetic field may enhance the magnitude of the nuclear magnetic resonance signal. In addition, the present invention utilizes a nanowire as a magnetic gradient source, which may achieve the integration of the magnetic gradient source, the detector and the radio-frequency source on a same chip; and since it completely adopts electrical signals for reading, the post-system thereof has a high integration level.

ILLUSTRATIONS OF REFERENCE NUMERALS

1 nanowire-magnetic gradient source
2 radio-frequency source
3 static magnetic source
4 nano-scale superconducting quantum interference device
5 test sample
6 nanomagnet-magnetic gradient source
7 resonant curved surface
8, 9 nanowire
10 arbitrary waveform generator
11 attenuator
12 preamplifier
13 data acquisition system
14 programmable logic circuit
15, 17 electric current source
16 tickler coil
18 radio-frequency oscillator
19 modulator
20 pulse signal generator
21 power amplifier
B magnetic gradient source
C NanoSQUID measurement loop

DETAILED DESCRIPTION OF THE PREFERRED EMBODIMENTS

The embodiment modes of the present invention are described hereunder through specific examples, and persons skilled in the art may easily understand other advantages and efficacies of the present invention from the contents disclosed in the present description. The present invention may be further implemented or applied through other different specific embodiment modes, and various modifications or amendments may also be made to each of the details in the present description based on different perspectives and applications without departing from the spirit of the present invention.

Please refer to FIG. 1 to FIG. 7. It is to be noted that the drawings provided in the present embodiment only explain the basic conception of the present invention in an illustrative manner, so the drawings only display the components relevant to the present invention rather than being drawn according to the number, shape and size of the components during actual implementation, the shape, number and scale of each component may be randomly changed during its actual implementation, and the layout of the components thereof might also be more complicated.

Embodiment 1

The present invention provides a magnetic resonance imaging method, which at least comprises the following steps of:

placing a test sample within an action range of a magnetic gradient source and a nano-scale superconducting quantum interference device, applying a static magnetic field on the test sample by a static magnetic source, and applying a nuclear magnetic resonance radio-frequency pulse on the test sample by a radio-frequency source to excite the test sample to cause nuclear magnetic resonance;

directly coupling the nano-scale superconducting quantum interference device with the test sample to detect nuclear magnetic resonance spectrum signals generated by the test sample;

establishing the image of the test sample according to the detected nuclear magnetic resonance spectrum signals.

Specifically, an action range of the magnetic gradient source refers to the space range where its generated gradient magnetic field locates, and the action range of the nano-scale superconducting quantum interference device refers to its detectable space range, i.e., the scope that is coupleable with the spins of the test sample. The test sample is placed within the overlap region of the action range therebetween.

Specifically, the test sample may be in solid or liquid form or the like, the nano-scale superconducting quantum interference device is taken as a detector of the nuclear magnetic resonance spectrum signals of the magnetic resonance, to directly and close-range detect the spins of the test sample by the magnetic flux couplings, so as to obtain the nuclear magnetic resonance spectrum signals generated by the nuclear spins. The distance between the nano-scale superconducting quantum interference device and the test sample is preferably less than 100 nm, and the test sample may be directly contact with the nano-scale superconducting quantum interference device.

The static magnetic source may be a permanent magnet, a solenoid magnet or a superconducting magnet, which is used for forming a static magnetic field for the magnetic nuclear resonance of the test sample in the imaging region where the test sample locates. As an example, the magnitude of the magnetic field generated by the static magnetic source is 1~5 T (Tesla), certainly, the magnitude of the magnetic field generated by the static magnetic source may also be set as other values as required, but within the parallel critical magnetic field that the nanoSQUID can withstand.

The function of the radio-frequency source is to transmit a high frequency electromagnetic wave of magnetic resonance frequency to the test sample in the static magnetic field, to excite the nuclear magnetic resonance of the test sample. In the present embodiment, it may adopt a continuous radio-frequency source, use a mixer or modulator, to combine with a baseband signal to form a combined nuclear magnetic resonance pulse to excite the test sample.

If there is only a uniform static magnetic field $B_0$, the Larmor frequencies of the spins of the test sample are the same everywhere, and the resonant signals generated under the action of radio-frequency pulse magnetic field are the same as well, thus it is unable to distinguish the generated signals everywhere, and unable to obtain the magnetic resonant image as well. Therefore, it requires to overlap a magnetic field gradient with the static magnetic field $B_0$, and the direction of the magnetic field intensity of the gradient magnetic field is same to the direction of the static magnetic field $B_0$, with its magnitude linearity varies with the space position. According to the Larmor formula, the precession frequency ω of the magnetization intensity of the sample also continuously varies with the position coordinates of the gradient direction. In the present invention, the gradient magnetic field is introduced by the magnetic gradient source, to continuously vary the space distribution of the magnetic field, after that, each resonant region is excited point by point by using a frequency-sweep method or field-sweep method. Wherein, fixing magnetic field strength, and generating resonance by continuously varying the frequency of electromagnetic radiation of the radio-frequency source is called as the frequency-sweep method; while fixing the electromagnetic radiation frequency, and generating resonance by continuously varying the strength of the static magnetic field is called as the field-sweep method. The present invention fixes the position by scanning the frequency of the magnetic field or the radio-frequency magnetic field, to instantly obtain the nuclear magnetic resonance spectrum signals in a resonance region, and the height of the resonance peak is the imaging contrast ratio at this point.

In the present invention, each resonant region limited by the gradient magnetic fields has a size within 1~100 nm, that is, the final magnetic resonance imaging resolution is 1~100 nm.

Figure 1:
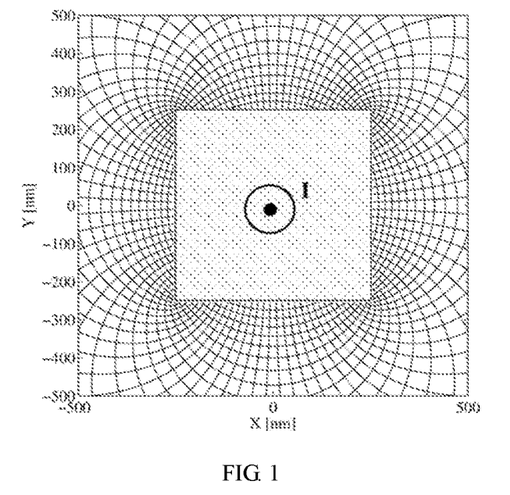
FIG. 1 is a schematic diagram showing electric current passing through a nanowire to form magnetic field gradients $G_{xy}$ and $G_{yx}$ to divide the space into a grid-like pattern.

Specifically, the magnetic gradient source may be generated by the current flowing through the nanowire, wherein the nanowire has a width of 100 nm-1 μm. According to Ampere's rule, if electric current I passes through the nanowire, it may generate a circulating magnetic field around the wire; because that the nanowire features a very small diameter, the nanowire of 1 milliampere may generate a gradient magnetic field of about 1 mT/nm within a small scope around. Since the magnetic field is a vector, which has a vector $B_x$ and $B_y$ along the x direction and y direction respectively (the direction of the static magnetic field is taken as the z direction, which is also referred to hereinafter), then derivations are taken versus its x direction and y direction to obtain $G_{xy}=dB_x/dy$, and $G_{yx}=dB_y/dx$, which are two mutually perpendicular gradient tensors. The $G_{yx}$ may be used to label the space position information of the static magnetic field in the x direction, and the $G_{xy}$ may be used to label the space information of the radio-frequency magnetic field in the y direction; or the $G_{yx}$ may be used to label the space information of the radio-frequency magnetic field in the x direction, and the $G_{xy}$ may be used to label the space information of the static state magnetic field in the y direction, so as to form the grid as shown in FIG. 1, and form the image by positioning the spin information in each grid by the nuclear magnetic resonance. The advantage of the magnetic gradient source is that it may generate a relative large magnetic gradient, and it may quick switch, and may be combined with the spin polarization controlled pulse for synchronous usage.

It should be pointed out that, the magnetic gradient source may generate a three-dimensional gradient magnetic field or a two-dimensional gradient magnetic field as required, so as to obtain a three-dimensional image or a two-dimensional image. FIG. 1 shows a two-dimensional grid-like gradient magnetic field, which is generated by a nanowire; in another embodiment, it may generate a three-dimensional gradient magnetic field by two nanowires of cross-shaped arrangement, to form a whole space gradient tensor, which has components of $G_{yx}$, $G_{xy}$, $G_z$ along x, y, z directions respectively, wherein the $G_{yx}$ may label the space position information of the static magnetic field in the x direction; the $G_{yx}$ may label the space information of the radio-frequency magnetic field in the y direction (or the $G_{yx}$ may label the space information of the radio-frequency magnetic field in the x direction, and the $G_{xy}$ may label the space information of the static state magnetic field in the y direction); $G_z$ may label the space position information of the static magnetic field in the z direction.

Figure 2:
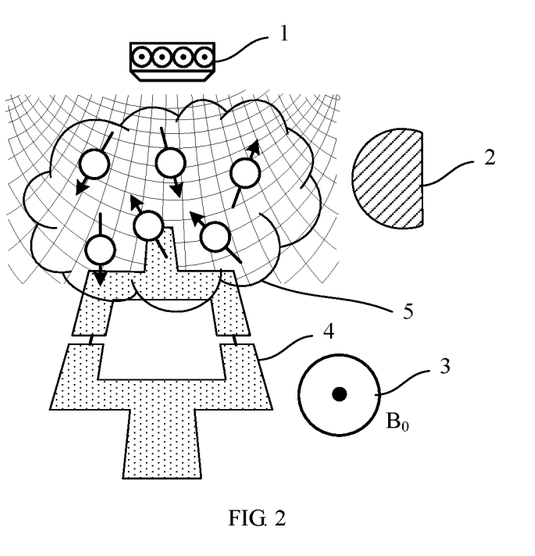
FIG. 2 is a schematic diagram of a magnetic resonance imaging by taking the nanowire as a magnetic gradient source.
Figure 3:
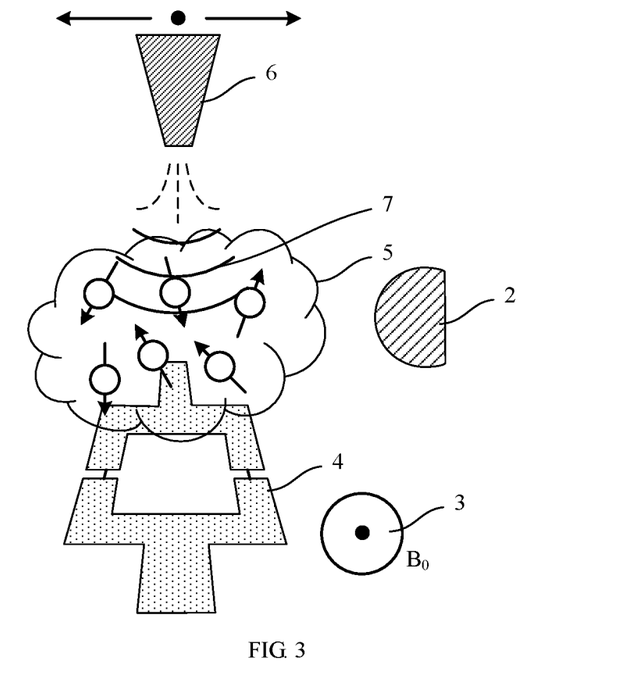
FIG. 3 is a schematic diagram of a magnetic resonance imaging by taking a nanomagnet as a magnetic gradient source.

Please refer to FIG. 2, it is shown to a schematic diagram of the magnetic resonance imaging by taking the nanowire as the magnetic gradient source. As shown in figure, the test sample 5 is placed between the nanowire-magnetic gradient source 1 and the nano-scale superconducting quantum interference device 4, and is located within the action range of the nanowire-magnetic gradient source 1 and the nano-scale superconducting quantum interference device 4; the static magnetic source 3 forms a static magnetic field $B_0$ in the space where the test sample locates, the radio-frequency source 2 excites the spins of the test sample, to cause the nuclear magnetic resonance. The nano-scale superconducting quantum interference device 4 directly and close-range detect the spin of the test sample by the magnetic flux coupling, which is not influenced by vibrations and electric field.

In another embodiment, the magnetic gradient source may adopt a nanomagnet, and the nanomagnet has an end size of 100 nm~1 um. According to the magnetic field distribution around the nanomagnet, it may also serve as an analogous large gradient source, while, although the gradient source fails to quick switch and only labels the space position information of the static magnetic field, it is able to limit the resonant region in a very thin curved surface, and a fine scan stepper motor of a scanning probe microscopy can be used to scan the relative location of the nanomagnet and the test sample, thus the intersecting cross section of the resonant curved surface and the test sample scans the inside of the test sample to obtain the position information of the spin distribution. Please refer to FIG. 3, it is shown to a schematic diagram of the magnetic resonance imaging by taking the nanomagnet as the magnetic gradient source. As shown in figure, the nanomagnet-magnetic gradient source 6 decreases continuously in size from top to bottom, to form an end portion of small size. The nanomagnet-magnetic gradient source 6 makes the resonant curved surface 7 scan the inside of the test sample 5 by continues moving and scanning to obtain the position information of the spin distribution.

In the present invention, it may achieve a large gradient magnetic field by using the nanowire or nanomagnet as the magnetic gradient source, wherein the magnetic gradient scope generated by the magnetic gradient source is preferably 0.05~5 mT/nm, and limits the size of each resonant region within a range of 1~100 nm, so that the large magnetic field gradient may enhance the magnetic resonance imaging resolution.

The principle of the present invention that the nano-scale superconducting quantum interference device 4 is taken as a detector to achieve the magnetic resonance imaging of a nano-scale resolution is that: the image of the magnetic resonance imaging may be considered to be formed by single volumetric pixel, wherein the smaller the single volumetric pixel is, the larger the resolution of the image is. The nano-scale resolution means that the corresponding actual space volume of the volumetric pixel needs to achieve a nano-scale size, thus it requires that the detector may have a sufficient sensitivity to detect the nuclear magnetic resonance (NMR) spectrum signals generated by the nuclear spin within a nano-scale volume, and the height of the resonance peak in the spectrum is the contrast ratio of the volumetric pixel. Because of the sensitivity of the nano-scale superconducting quantum interference device, currently, it may detect one single electron spin, which corresponds to that the size of the volumetric pixel is about 3~5 cubic nanometer. The frequency of the resonant peak of the NMR spectrum has a one-to-one correspondence with the magnitude of the magnetic field, the introduction of the gradient magnetic field continuously varies the space distribution of the magnetic field, as such, the position of the NMR resonant peak corresponds to the space position of the volumetric pixel. It may fix the position by scanning the frequency of the magnetic field or the radio-frequency magnetic field, to instantly obtain the nuclear magnetic resonance spectrum signals in the volumetric pixel (or resonant region). Generally, due to the inherent attribute of the test sample, there exists a width of the NMR resonant peak, and during the magnetic resonance imaging, the size of the volumetric pixel is proportional to the width of the NMR resonant peak and is inversely proportional to the magnetic field gradient. For example, with regard to a peak width of 42 kHz, it requires a magnetic field gradient of about 1 mT/nm to achieve the volumetric pixel of 1 nm. Therefore, it may enhance the magnetic resonance imaging resolution by adopting a large gradient magnetic field. According to the space distribution of the magnetic field gradient, and by revivifying the NMR signal of the volumetric pixel to the space position, it may obtain the magnetic resonance imaging of nano-scale resolution.

Specifically, the nano-scale superconducting quantum interference device (nanoSQUID) is used to detect the spins on the basis of a critical electric current-magnetic flux modulation curve. Since the superconducting transition of the nanoSQUID is a probabilistic transition process, the actual measurement is to count its superconducting transition probability, that is, by inputting a set number of bias current pulses, and by counting a sum of the transition voltage pulses, the transition probability is obtained. Wherein the corresponding electric current pulse magnitude with a transition probability of 50% is defined as a critical electric current. When inputting the electric current pulse of the critical electric current magnitude, the nanoSQUID is worked at the operating point (the center region of the flux modulation of the device).

In the present invention, the method for detecting the nuclear magnetic resonance spectrum signals generated by the test sample by using the nano-scale superconducting quantum interference device is that: inputting a predetermined current pulse to the nano-scale superconducting quantum interference device to make it work at a critical point of the superconducting transition, and work at the operating point; if the nuclear magnetic resonance spectrum signals of the test sample is coupled to the nano-scale superconducting quantum interference device, magnetic flux will be changed, to deviate the nano-scale superconducting quantum interference device from the operating point; then using a programmable logic circuit to perform a PID feedback logic operation, and applying a feedback signal on the nano-scale superconducting quantum interference device through a feedback coil controlled by a current source, to fix the nano-scale superconducting quantum interference device back to the operating point; then obtaining the nuclear magnetic resonance spectrum signals of the test sample by measuring feedback quantity of the feedback circuit.

Specifically, the programmable logic device may adopt a field programmable gate array (FPGA). FPGA is a novel programmable logic device appeared in the 80's of the 20th century, with a structure differing from the device based on the and-or array. The most important feature of the FPGA is that a field program is realizable, wherein the so-called field program refers to achieving logical reconstruction on the chip that has been welded on the PCB or is at work, certainly, it may also change the logic after working for a while. Besides FPGA, in-system programmable integrated circuits, such as ispLSI based on the series of GAL, may also have such function. PID (proportional-integral-derivative) feedback logic operation is realizable by a PID controller, wherein a PID control consists of a proportional unit P, an integral unit I and a derivative unit D, and is a commonly used feedback loop component in the industrial control. The PID controller compares the collected data with a reference value, and the difference therebetween is used for calculating a new input value, while the object of the new input value is to make the data of the system reach or keep at the reference value. Differing from other simple control calculations, the PID controller may adjust the input value according to occurrence rates of the historical data and differences, by which the system may be more accuracy and more stable. The present invention utilizes the programmable logic circuit to perform the PID feedback logic operation, and make the nano-scale superconducting quantum interference device always work at the operating point, wherein the feedback quantity of the feedback circuit reflects the variable signals of the spin polarization of the test sample, i.e., the nuclear magnetic resonance spectrum signals generated by the nuclear spins.

Figure 4:
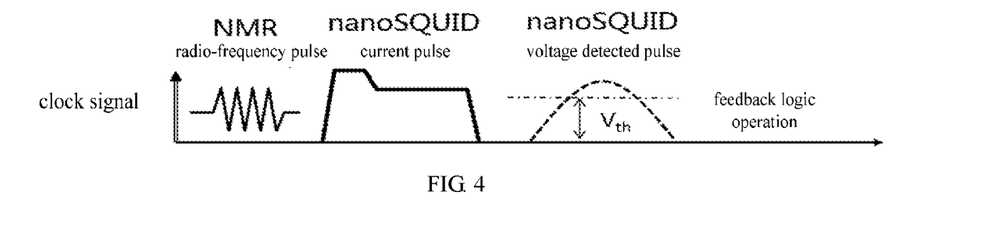
FIG. 4 is a schematic diagram of a pulse sequence when detecting a nuclear magnetic resonance signal by a nano-scale superconducting quantum interference device.

Please refer to FIG. 4, it is shown to a schematic diagram of a pulse sequence when detecting a nuclear magnetic resonance signal by a nano-scale superconducting quantum interference device, wherein, firstly, the radio-frequency source sends out a nuclear magnetic resonance (NMR) radio-frequency pulse, then, the nanoSQUID works at the operating point by the nanoSQUID electric current pulse, and the nanoSQUID is detected whether it is working at the operating point by using the nanoSQUID voltage detected pulse Vth, and the nanoSQUID is fixed back to the operating point by the FPGA feedback logic operation. It should be pointed out that, the waveform in FIG. 4 is simply an example, other waveforms may also be adopted as required, which should not be taken as limiting the scope of the invention herein.

The magnetic resonance imaging method of the present invention adopts the nano-scale superconducting quantum interference device as a detector, which may achieve magnetic resonance imaging of nano-scale resolution, and measurement is not influenced by vibrations and electric signals; the sample may be directly close-coupled with the detector, the imaging range is enlarged, and the invention can be performed under the strong magnetic field condition; while on the assumption that the number of spins is constant, the strong magnetic field may enhance the magnitude of the NMR signal, so as to obtain a good imaging quality. The radio-frequency source and the detector may be integrated on a same chip, if the nanowire is used as the magnetic gradient source, it may achieve the integration of the magnetic gradient source, the radio-frequency source and the detector on a same chip, and electrical signals are adopted for the reading, the post-system thereof has a high integration level. The magnetic resonance imaging method of the present invention has high resolution, which may achieve 1~100 nm, and may be used for detecting the microscopic world; moreover, the present invention may directly and close-range detect the sample, wherein the coupling distance between the detector and the test sample is less than 100 nm, or the detector directly contacts with the test sample.

Embodiment 2

The present invention further provides a magnetic resonance imaging apparatus, comprising:

a static magnetic source, for forming a static magnetic field in a space where the test sample locates;

a radio-frequency source, for exciting the nuclear magnetic resonance of the test sample;

a magnetic gradient source, for forming a gradient magnetic field in the space where the test sample locates;

a detector, which is a nano-scale superconducting quantum interference device, for directly coupling the test sample to detect nuclear magnetic resonance spectrum signals generated by nuclear spins of the test sample;

an image forming apparatus, for constructing an image of the test sample according to the nuclear magnetic resonance spectrum signals detected by the detector.

Specifically, the magnetic gradient source is a nanowire or nanomagnet. The superconducting ring of the nano-scale superconducting quantum interference device has an area less than 1 $\mu m^2$.

Figure 5:
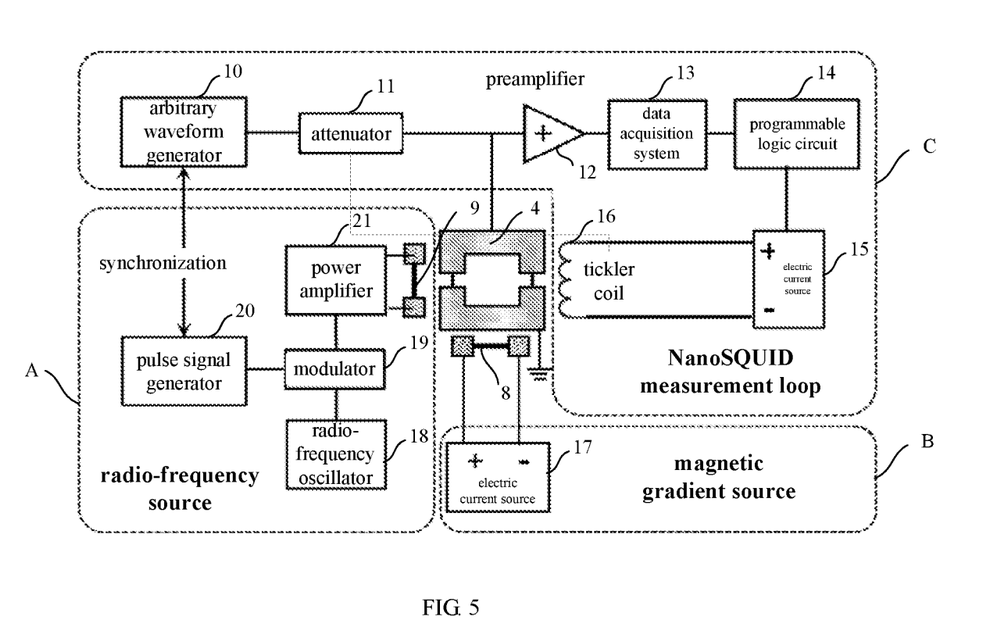
FIG. 5 is a structural schematic diagram of a specific embodiment of the magnetic resonance imaging apparatus of the present invention.

Please refer to FIG. 5, it is shown to a structural schematic diagram of a specific embodiment of the magnetic resonance imaging apparatus of the present invention, comprising a radio-frequency source A, a magnetic gradient source B and a NanoSQUID measurement loop C. It should be pointed out that, the static magnetic source and the image forming apparatus are not shown in the figure.

Specifically, The radio-frequency source A consists of a radio-frequency oscillator 18, a modulator 19, a pulse signal generator 20, a power amplifier 21 and a nanowire 9, Wherein, the radio-frequency oscillator 18 is connected with the modulator 19, and is combined with the baseband signal sent out by the pulse signal generator 20 to form the isopulse combination in the nuclear magnetic resonance, such as inversion-recovery or spin echo, which is further enlarged by the power amplifier 21, and sent out through the nanowire 9, to excite the nuclear magnetic resonance of the test sample.

The magnetic gradient source B consists of a electric current source 17 and a nanowire 8, wherein the nanowire 8 has a width of 100 nm~1 μm, and the nanowire 8 is applied with electric current by the electric current source 17, to generate a circulating magnetic field around the nanowire 8, so as to form a large gradient magnetic field, with a magnetic field gradient up to 0.05~5 mT/nm.

The NanoSQUID measurement loop C consists of a nano-scale superconducting quantum interference device 4, an arbitrary waveform generator 10, an attenuator 11, a preamplifier 12, a data acquisition system 13, a programmable logic device 14, an electric current source 15 and a tickler coil 16. The nano-scale superconducting quantum interference device 4 is used as a detector, which comprises a planar superconducting structure and at least one nanowire formed on the surface of the planar superconducting structure, to form two parallel nano-junctions, to construct a superconducting loop, i.e., the superconducting ring. The measurement loop C is divided into two channels, in one channel, the arbitrary waveform generator 10 sends out a predetermined electric current pulse, which pass though the attenuator 11 and is applied on the nano-scale superconducting quantum interference device 4, to make it work at the operating point (the center region of the flux modulation of the device); in another channel, the preamplifier 12 enlarges the voltage detected pulse signal of the nano-scale superconducting quantum interference device 4, and the enlarged signal is collected by the data acquisition system 13, a feedback logic operation is performed by the programmable logic circuit 14, so that the electric current source 15 generates electric current of specific magnitude which is further applied on the tickler coil 16, wherein the tickler coil 16 acts on the nano-scale superconducting quantum interference device 4, to fix it back to the operating point.

Specifically, the arbitrary waveform generator 10 is one kind of annunciators, and has all the features of the annunciator. It mainly provides the required known signals (various kinds of waveforms) for the test circuit, and detects interested parameters by other instruments. The arbitrary waveform generator 10 is synchronous with the pulse signal generator 10 by the high-accuracy clock signal set in the pulse signal generator 20, so that the NMR radio-frequency pulse is synchronous with the nanoSQUID electric current pulse and the nanoSQUID voltage detected pulse, to obtain the NMR spectrum signal in the resonant region by scanning the frequency of the magnetic field or the radio-frequency magnetic field.

The magnetic resonance spectrum signals of the test sample can be obtained by the feedback quantity of the feedback loop, and an image of the test sample is constructed by the image forming apparatus by the nuclear magnetic resonance spectrum signals detected by the detector, Wherein, it may obtain the space position information of the volumetric pixel by the frequency of the resonant peak of the NMR spectrum, wherein the height of the resonant peak is the contrast ratio of the volumetric pixel.

Specifically, in the magnetic resonance imaging apparatus of the present invention, the nano-scale superconducting quantum interference device (nanoSQUID) is used to detect the spins on the basis of a critical electric current-magnetic flux modulation curve, The usage method of the magnetic resonance imaging apparatus of the present invention is that: inputting a predetermined current pulse to the nano-scale superconducting quantum interference device to make it work at an operating point; if the nuclear magnetic resonance spectrum signals of the test sample is coupled to the nano-scale superconducting quantum interference device, magnetic flux will be changed, to deviate the nano-scale superconducting quantum interference device from the operating point, then using a programmable logic circuit to perform a PID feedback logic operation, and applying a feedback signal on the nano-scale superconducting quantum interference device through a feedback coil controlled by a current source, to fix the nano-scale superconducting quantum interference device back to the operating point; obtaining the nuclear magnetic resonance spectrum signals of the test sample by measuring feedback quantity of the feedback circuit.

The present invention utilizes a programmable logic circuit to perform a PID feedback logic operation, to make the nano-scale superconducting quantum interference device always work at the operating point, wherein the feedback quantity of the feedback circuit reflects the variable signals of the spin polarization of the test sample, i.e., the nuclear magnetic resonance spectrum signals generated by the nuclear spin. The present invention further establishes an image of the test sample according to the detected nuclear magnetic resonance spectrum signals and space distribution information of gradient magnetic fields generated by the magnetic gradient source.

In the magnetic resonance imaging apparatus of the present invention, the radio-frequency source and the detector may be integrated on a same chip. If the nanowire is used as the magnetic gradient source, it may achieve the integration of the magnetic gradient source, the radio-frequency source and the detector on a same chip, and electrical signals are adopted for the reading, the post-system thereof has a high integration level. The magnetic resonance imaging apparatus of the present invention has high resolution, which may achieve 1~10 nm, and may be used for detecting the microscopic world, moreover, the present invention may directly and close-range detect the sample, wherein the coupling distance between the detector and the test sample is less than 100 nm, or the detector directly contacts with the test sample.

Embodiment 3

Figure 6:
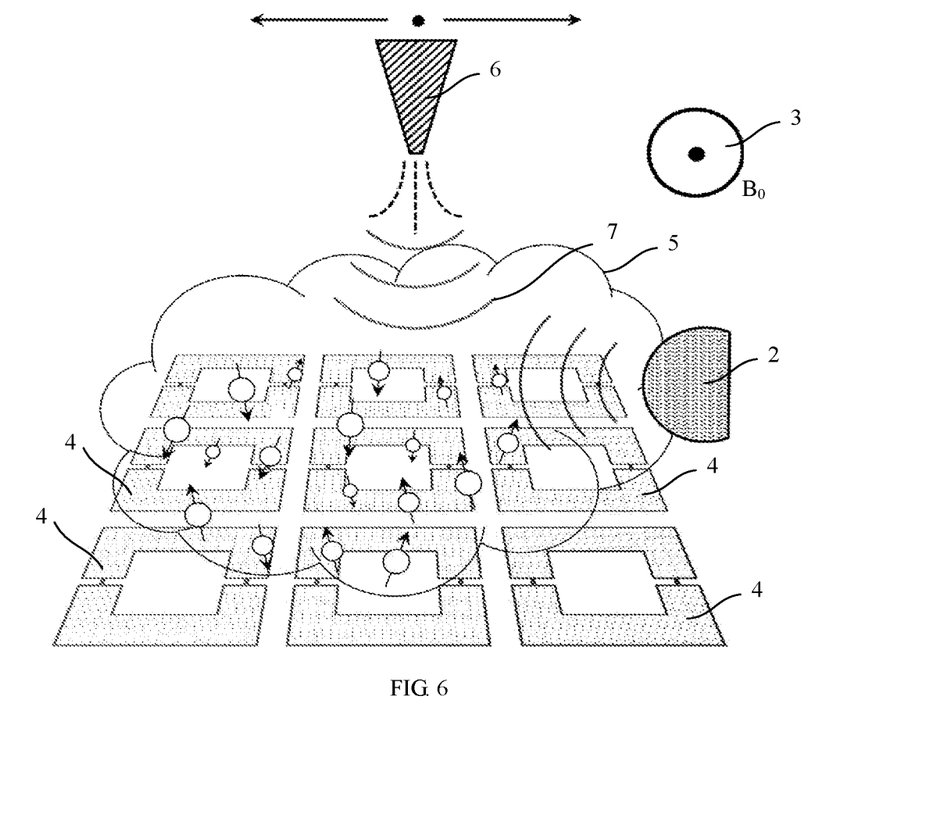
FIG. 6 is a schematic diagram of the magnetic resonance imaging when adopting the nanomagnet-magnetic gradient source and taking a nanoSQUID array as a detector.

If the size of the test sample is larger than that of the nano-scale superconducting quantum interference device, the single magnetic resonance imaging apparatus may only partly image the sample. If it requires to image the overall structure, it may arrange the nano-scale superconducting quantum interference device into an array, and image each part of the test sample according to the methods in embodiments 1 and 2, respectively, then finally integrate the images into a overall image. FIG. 6 is a schematic diagram of the magnetic resonance imaging when adopting the nanomagnet-magnetic gradient source and taking a nano-scale superconducting quantum interference device array as a detector of the nuclear magnetic resonance spectrum signals, wherein for clarity, the lead line of the nanoSQUID is omitted, and its measurement loop is same to the measurement loop of the magnetic resonance imaging apparatus when adopting a single nanoSQUID as the detector. According to measurement requirements, it requires to establish an individual measurement channel for each nanoSQUID, and the specific imaging method, principle and apparatus of each measurement channel are same to that of each imaging apparatus for imaging, which is not detailed herein again.

Embodiment 4

The present embodiment adopts basically the same technical solution as in the embodiment 3, with the distinguishing feature in that, the embodiment 1 adopts a nanomagnet-magnetic gradient source to position the spins inside the test sample, while the present embodiment adopts a nanowire-magnetic gradient source to position the spins inside the test sample.

Figure 7:
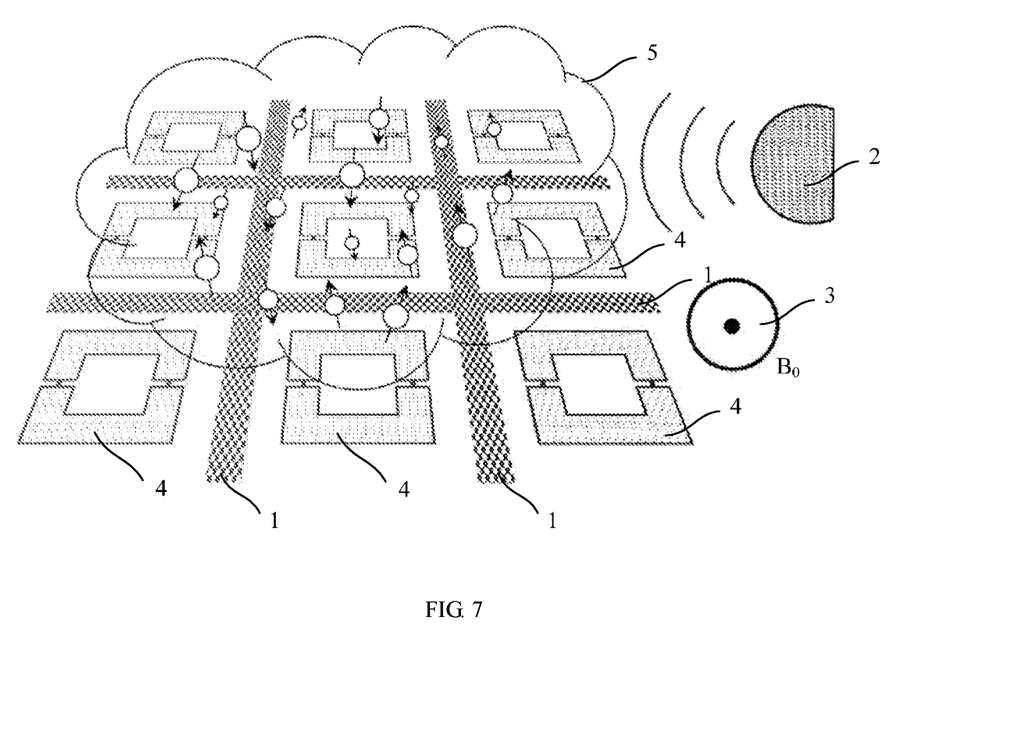
FIG. 7 is a schematic diagram of the magnetic resonance imaging when adopting the nanowire-magnetic gradient source and taking a nanoSQUID array as a detector.

Please refer to FIG. 7, it is shown to a schematic diagram of the magnetic resonance imaging when adopting the nanowire-magnetic gradient source and taking a nano-scale superconducting quantum interference device array as a detector of the nuclear magnetic resonance spectrum signals, Wherein, the nanowire-magnetic gradient source and the nano-scale superconducting quantum interference device are integrated on a same chip, and the nanowire-magnetic gradient source is located within the nano-scale superconducting quantum interference device array. Wherein, the horizontal nanowire-magnetic gradient source may be connected with the vertical nanowire-gradient source, or may be not.

It may image each part of the test sample step-by-step by adopting the nano-scale superconducting quantum interference device array as the detector of the nuclear magnetic resonance spectrum signals, and further integrate to obtain the overall image of the test sample, which is not only applicable for a high-resolution imaging of a microsample, but also applicable for a high-resolution imaging of large sized sample.

From the above, the magnetic resonance imaging method and apparatus of the present invention have the following beneficial effects that: the present invention adopts the nano-scale superconducting quantum interference device (nanoSQUID) as a detector for the nuclear magnetic resonance (NMR) spectrum signal in the magnetic resonance imaging (MRI), to achieve the magnetic resonance imaging of nano-scale resolution. Because the area of the superconducting ring of the nano-scale superconducting quantum interference device is relative small, the device is not susceptible to the disturbance of external magnetic field, vibrations and electric signals, and is not need for individual magnetic shielding isolation; the test sample may be directly and close-range coupled with the detector or directly contacted with the detector, and together cooled to below its superconductor temperature, by which the imaging scope is relative large, and the performance for characterizing magnetic properties of the microscopic sample and detecting the microscopic spin is prominent, and thus the measurement sensitivity for single electron spin is achievable. Meanwhile, the nano-scale superconducting quantum interference device can withstand a relative large parallel critical magnetic field because of its planar structure, and can work in a strong magnetic field; while on the assumption that the number of spins is constant, the strong magnetic field may enhance the magnitude of the nuclear magnetic resonance signal. In addition, the present invention utilizes a nanowire as a magnetic gradient source, which may achieve the integration of the magnetic gradient source, the detector and the radio-frequency source on a same chip; and since it completely adopts electrical signals for reading, the post-system thereof has a high integration level. Therefore, the present invention effectively overcomes a variety of disadvantages in the prior art and has high industrial utility value.

The abovementioned embodiments only illustratively describe the principle and efficacy of the present invention, rather than being used to limit the present invention. Any person skilled in the art may modify or amend the abovementioned embodiments without departing from the spirit and scope of the present invention. Thus, all equivalent modifications or amendments accomplished by persons having common knowledge in the technical field concerned without departing from the spirit and technical thoughts revealed by the present invention shall still be covered by the claims of the present invention.

What is claimed is:

1. A magnetic resonance imaging method comprising the following steps of:

placing a test sample within an action range of a magnetic gradient source and a nano-scale superconducting quantum interference device, applying a static magnetic field on the test sample by a static magnetic source, and applying a nuclear magnetic resonance radio-frequency pulse on the test sample by a radio-frequency source to excite the test sample to cause nuclear magnetic resonance;

directly coupling the nano-scale superconducting quantum interference device with the test sample to detect nuclear magnetic resonance spectrum signals generated by the test sample by the following steps of:

inputting a predetermined current pulse to the nano-scale superconducting quantum interference device to make it work at an operating point;

coupling the nano-scale superconducting quantum interference device with the test sample to make the nano-scale superconducting quantum interference device a deviation from the operating point as magnetic flux changing;

using a programmable logic circuit to perform a proportional-integral-derivative (PID) feedback logic operation, fixing the nano-scale superconducting quantum interference device back to the operating point by applying a feedback signal on the nano-scale superconducting quantum interference device through a current source controlled feedback circuit; and obtaining the nuclear magnetic resonance spectrum signals of the test sample by measuring feedback quantity of the feedback circuit; and establishing an image of the test sample according to the detected nuclear magnetic resonance spectrum signals and space distribution information of gradient magnetic fields generated by the magnetic gradient source.

2. The magnetic resonance imaging method according to claim 1, characterized in that: the method for exciting the test sample by the radio-frequency source is that: adopting a continuous radio-frequency source and using a mixer or modulator, to combine with a baseband signal to form a combined nuclear magnetic resonance pulse, and generating a radio-frequency magnetic field at a radio-frequency source terminal to excite the test sample.

3. The magnetic resonance imaging method according to claim 1, characterized in that: position measurement is performed by scanning a frequency of the static magnetic field or the radio-frequency magnetic field, to instantly obtain the nuclear magnetic resonance spectrum signals in a resonance region.

4. The magnetic resonance imaging method according to claim 1, characterized in that: the magnetic gradient generated by the magnetic gradient source is 0.05~5 mT/nm.

5. The magnetic resonance imaging method according to claim 1, characterized in that: a distance between the nano-scale superconducting quantum interference device and the test sample is less than 100 nm.

6. The magnetic resonance imaging method according to claim 1, characterized in that: the magnetic gradient source is obtained by a current flowing through a nanowire, and the nanowire has a width of 100 nm~1 μm.

7. The magnetic resonance imaging method according to claim 1, characterized in that: the magnetic gradient source is a nanomagnet, and the nanomagnet has an end size of 100 nm~1 μm.

8. The magnetic resonance imaging method according to claim 1, characterized in that: the magnetic gradient source generates a three-dimensional gradient magnetic field or a two-dimensional gradient magnetic field.

9. A magnetic resonance imaging apparatus comprising:
a static magnetic source, for forming a static magnetic field in a space where the test sample locates;
a radio-frequency source, for exciting the nuclear magnetic resonance of the test sample;
a magnetic gradient source, for forming a gradient magnetic field in the space where the test sample locates;
a detector, which is a nano-scale superconducting quantum interference device, for directly coupling the test sample to detect the nuclear magnetic resonance spectrum signals generated by nuclear spins of the test sample;
an image forming apparatus, for constructing an image of the test sample according to the nuclear magnetic resonance spectrum signals detected by the detector;
wherein, the nano-scale superconducting quantum interference device detects the nuclear magnetic resonance spectrum signals generated by nuclear spins of the test sample by the following steps of:
inputting a predetermined current pulse to the nano-scale superconducting quantum interference device to make it work at an operating point;
coupling the nano-scale superconducting quantum interference device with the test sample to make the nano-scale superconducting quantum interference device a deviation from the operating point as magnetic flux changing;
using a programmable logic circuit to perform a proportional-integral-derivative (PID) feedback logic operation, fixing the nano-scale superconducting quantum interference device back to the operating point by applying a feedback signal on the nano-scale superconducting quantum interference device through a current source controlled feedback circuit; and
obtaining the nuclear magnetic resonance spectrum signals of the test sample by measuring feedback quantity of the feedback circuit.

10. The magnetic resonance imaging apparatus according to claim 9, characterized in that: the magnetic gradient source is a nanowire or nanomagnet.

11. The magnetic resonance imaging apparatus according to claim 10, characterized in that: the magnetic gradient source is a nanowire; the magnetic gradient source, the radio-frequency source and the detector are integrated on a same chip.

12. The magnetic resonance imaging apparatus according to claim 9, characterized in that: a superconducting ring of the nano-scale superconducting quantum interference device has an area less than 1 μm$^2$.

13. The magnetic resonance imaging apparatus according to claim 9, characterized in that: the magnetic resonance imaging apparatus has a resolution of 1~100 nm.

14. The magnetic resonance imaging apparatus according to claim 9, characterized in that: the coupling distance between the detector and the test sample is less than 100 nm.

15. The magnetic resonance imaging method according to claim 1, wherein the predetermined current pulse which makes the nano-scale superconducting quantum interference device to work at the operating point is determined by the following steps of:
inputting a set number of bias current pulses,
counting a number the switching voltage pulses,
calculating the switching probability,
the current pulses with a switching probability of 50% is the predetermined current pulse.

* * * * *